(12) United States Patent
Venkatraman et al.

(10) Patent No.: US 10,835,514 B2
(45) Date of Patent: Nov. 17, 2020

(54) DRY POWDER INHALER COMPOSITIONS OF 7-AZONIABICYCLO[2.2.1]HEPTANE DERIVATIVES

(71) Applicant: THERON PHARMACEUTICALS, INC., Sunnyvale, CA (US)

(72) Inventors: Meenakshi S. Venkatraman, Sunnyvale, CA (US); Xiaoming Zhang, Sunnyvale, CA (US); Phillip Haywood, Hertfordshire (GB)

(73) Assignee: THERON PHARMACEUTICALS, INC., Sunnyvale, CA (US)

( * ) Notice: Subject to any disclaimer, the term of this patent is extended or adjusted under 35 U.S.C. 154(b) by 0 days.

(21) Appl. No.: 16/067,113

(22) PCT Filed: Jan. 7, 2017

(86) PCT No.: PCT/US2017/012650
§ 371 (c)(1),
(2) Date: Jun. 28, 2018

(87) PCT Pub. No.: WO2017/120559
PCT Pub. Date: Jul. 13, 2017

(65) Prior Publication Data
US 2019/0298690 A1    Oct. 3, 2019

Related U.S. Application Data

(60) Provisional application No. 62/276,778, filed on Jan. 8, 2016.

(51) Int. Cl.
| | | |
|---|---|---|
| A61K 9/14 | (2006.01) |
| A61P 11/06 | (2006.01) |
| A61K 31/40 | (2006.01) |
| A61K 31/403 | (2006.01) |
| A61K 9/00 | (2006.01) |
| A61K 31/58 | (2006.01) |
| A61K 47/26 | (2006.01) |
| C07D 487/08 | (2006.01) |

(52) U.S. Cl.
CPC .......... *A61K 31/403* (2013.01); *A61K 9/0075* (2013.01); *A61K 9/14* (2013.01); *A61K 31/40* (2013.01); *A61K 31/58* (2013.01); *A61K 47/26* (2013.01); *A61P 11/06* (2018.01); *C07D 487/08* (2013.01)

(58) Field of Classification Search
CPC ...... A61K 9/0075; A61K 9/14; A61K 31/403; A61K 31/58; A61K 47/26
See application file for complete search history.

(56) References Cited

U.S. PATENT DOCUMENTS

| | | | |
|---|---|---|---|
| 8,742,131 B2 * | 6/2014 | Pfister | C07D 487/08 548/411 |
| 8,742,134 B2 | 6/2014 | Pfister et al. | |
| 2007/0202054 A1 | 8/2007 | Pipkin et al. | |
| 2015/0157567 A1 * | 6/2015 | Cifter | A61K 45/06 424/451 |

FOREIGN PATENT DOCUMENTS

| | | | | |
|---|---|---|---|---|
| WO | WO-9841193 A1 * | 9/1998 | | A61K 9/0075 |
| WO | WO 2007/022351 A2 | 2/2007 | | |
| WO | WO 2011/094434 A2 | 8/2011 | | |
| WO | WO 2017/120559 A1 | 7/2017 | | |

OTHER PUBLICATIONS

Berkenfeld et al. (AAPS PharmSciTech Jun. 2015;16(3):479-490) (Year: 2015).*
Mosby's Respiratory Care Equipment 2013 Elsevier Health Sciences Cairo, J.M. p. 179 (Year: 2013).*
Le et al. (AAPS PharmSciTech 2012;13(2):477-484) (Year: 2012).*
PCT/US2017/012650 International Search Report and Written Opinion dated Apr. 12, 2017.
PCT/US2017/012650 International Preliminary Report of Patentability dated Jul. 10, 2018.
EP 17736492.4 Extended European Search Report dated Jul. 23, 2019.

* cited by examiner

*Primary Examiner* — Ernst V Arnold
(74) *Attorney, Agent, or Firm* — Alston & Bird LLP (57) ABSTRACT

Pharmaceutical compositions of muscarinic acetylcholine receptor antagonists suitable for administration via a dry powdered inhaler and methods of using the compositions for treating respiratory disease are provided.

20 Claims, 2 Drawing Sheets

DRY POWDER INHALER COMPOSITIONS OF 7-AZONIABICYCLO[2.2.1]HEPTANE DERIVATIVES

CROSS-REFERENCE TO RELATED APPLICATION

The present application is a national stage entry of PCT/US 17/12650 filed Jan. 7, 2017, which claims the benefit of U.S. 62/276,778 filed Jan. 8, 2016, incorporated by reference in its entirety for all purposes.

BACKGROUND

The number of people with respiratory conditions such as asthma and chronic obstructive pulmonary disease (COPD) continues to grow around the world. Asthma is a chronic respiratory disease that inflames and narrows the airways. Asthma causes recurring periods of chest tightness, shortness of breath, and coughing. Asthma affects approximately 7% of the population of the United States and causes approximately 4,210 deaths per year. COPD encompasses a variety of progressive health problems including chronic bronchitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five diseases as a world-wide health burden by the year 2020.

These respiratory conditions remain poorly controlled despite the availability of management guidelines and effective medication. One reason for poor control is incorrect use of inhaler devices. Pressurized metered-dose inhalers (pMDI) are the most frequently used devices worldwide, but many patients fail to use them correctly, even after repeated instruction. Dry powder inhalers (DPI), which are actuated by breathing alone to disburse drug particles to the lungs, are easier to use than pMDIs. However, only a few of the drugs effective for treatment of asthma or COPD have been formulated in a composition suitable for disbursement by a DPI, that is, in which a therapeutic dose can be delivered with reasonable uniformity throughout the device without excessive clumping of powder in the inhaling device.

Muscarinic acetylcholine receptors (mAChRs) are involved in numerous biological processes, such as asthma and chronic obstructive pulmonary disease (COPD). Inhaled anticholinergic therapy is currently considered the "gold standard" as first line therapy for COPD (Pauwels et al., Am. J. Respir. Crit. Care Med. 163, 1256 (2001)).

Despite the large body of evidence supporting the use of anticholinergic therapy for the treatment of respiratory diseases, relatively few anticholinergic compounds are available for use in the clinic for such indications. Of those that are, ipratropium (Atrovent; also as Combivent in combination with albuterol) is available in the United States only as a MDI formulation. Tiotropium (Spiriva) is available as a DPI formulation but only by itself and not as a combination treatment with corticosteroids. The lack of a co-formulation suitable for a DPI device appears to be due to the lack of sufficient chemical stability of tiotropium in the presence of other drugs. Additionally, tiotropium is extremely sensitive to moisture limiting its fine particle dose when packaged in gelatin capsules conventionally used for respiratory products.

SUMMARY OF THE CLAIMED INVENTION

The invention provides pharmaceutical composition comprising (a) a stereochemically pure M3 muscarinic acetylcholine receptor antagonist compound according to Formula I (as defined herein), and (b) lactose; wherein the compound of Formula I constitutes 0.025 to 4% by weight of the pharmaceutical composition and the compound of Formula I and lactose are in a blend, wherein the composition is dispersible from a dried powder inhaler. Preferably, the stereochemically pure M3 muscarinic acetylcholine receptor antagonist compound is selected from the group consisting of:

(1)

(1S,2R)-2-((R)-2'-cyclopentyl-2'-hydroxy-2'-phenylacetoxy)-7,7-dimethyl-7-azoniabicyclo[2.2.1]heptane bromide;

(2)

(1R,2S)-2-((R)-2'-cyclopentyl-2'-hydroxy-2'-phenylacetoxy)-7,7-dimethyl-7-azoniabicyclo[2.2.1]heptane bromide; and (3)

(1R,2R)-2-((R)-2'-cyclopentyl-2'-hydroxy-2'-phenylacetoxy)-7,7-dimethyl-7-azoniabicyclo[2.2.1]heptane bromide.

Alternatively, the Br anion may be replaced with another counterion preferably selected from the group consisting of chloride, iodide, sulfate, methanesulfonate, benzenesulfonate, and toluenesulfonate.

The lactose is preferably a sieved inhalation grade lactose, optionally with a particle diameter distribution characterized by an X10 of 9 μm, an X50 μm of 69 and an X90 of 141 μm. Optionally, the compound of Formula I has a particle diameter distribution characterized by an X90≤4.5 μm. Optionally, the particle diameter distribution is further characterized an X50≤2.5 μm. Optionally, the compound of Formula I constitutes 0.025 to 2.0% by weight of the composition. Optionally, the compound of Formula I constitutes 0.05% by weight.

The invention further provides a pharmaceutical composition as described above further comprising a corticosteroid, preferably mometasone. Optionally, the mometasone has a particle diameter distribution characterized by an X90 of ≤5 μm. Optionally, the mometasone has a particle distribution further characterized by an X50 of ≤2 μm. Optionally, the mometasone constitutes 2 to 5% by weight of the composition. Optionally, the relative standard deviation of particle diameter (RSD) is ≤5%. Optionally, the blend of compound of formula I in lactose has a fine particle fraction (FPF) of ≥30% or ≥50%. Optionally, the blend of mometasone in lactose has a fine particle fraction (FPF) of ≥30%. Optionally, the blend of mometasone in lactose has a fine particle fraction (FPF) of ≥50%. Optionally, the blend of compound of formula I and mometasone in lactose have a fine particle fraction (FPF) of ≥30%. Optionally, the blend of compound of formula I and mometasone in lactose have a fine particle fraction (FPF)≥50%.

Optionally, the mometasone constitutes 2.2% or 4.4% by weight of the composition. Optionally, the compound of Formula I constitutes 0.05% and mometasone 4.4% by weight of the composition. Optionally, the compound of Formula I constitutes 2.0% and mometasone 2.2% by weight of the composition.

Some compositions consist essentially of the compound of Formula I, lactose and optionally mometasone. Some compositions are free of any pharmaceutically acceptable carrier other than lactose. Some composition are stable for at least a month, six months or a year at ambient temperature.

The invention further provides a capsule comprising a pharmaceutical composition as previously defined, the capsule adapted for insertion in a dry powder inhaler wherein the composition can be dispersed into the lungs of a subject.

The invention further provides a dry powder inhaler comprising a pharmaceutical composition as previously described.

The invention further provides a process for preparing a pharmaceutical composition of claim 15, comprising: (a) micronizing a compound of Formula I until the volume mean diameter (VMD) is less than 5 μm, (b) blending the micronized compound of Formula I with lactose to make composition I, (c) micronizing mometasone until the VMD is less than 5 μm, (d) blending mometasone with lactose to make composition II, and (e) combining the blended compositions I and II to make a final blend. Optionally, the resulting pharmaceutical composition has a blend uniformity with a RSD≤5%. Optionally, the method also incorporates the composition into a dry powder inhaler.

The invention further provides a method of treating a patient with asthma or COPD comprising administering to the patient a therapeutically effective amount of a pharmaceutical composition as described above from a dry powder inhaler.

DEFINITIONS

An M3 muscarinic acetylcholine receptor antagonist is a compound having an $IC_{50}$ of less than 5, 3, 1, 0.5, or 0.3 nM, as measured by the muscarinic receptor radioligand binding assay described in Example 2 of U.S. Pat. No. 8,742,131.

"Alkyl" is a saturated linear, branched, cyclic, or a combination of linear and/or branched and/or cyclic hydrocarbon chain and/or ring of carbon atoms. In one embodiment, alkyl groups have between 1 and 12 carbon atoms, that is, $C_1$-$C_{12}$ alkyl. In another embodiment, alkyl groups have between 1 and 8 carbon atoms, that is, $C_1$-$C_8$ alkyl. The point of attachment of the alkyl group to the remainder of the molecule can be at any chemically feasible location on the fragment.

"Alkoxy" refers to the group —O-alkyl, for example, —O— $C_1$-$C_{12}$ alkyl or —O— $C_1$-$C_8$ alkyl.

"Lower alkyl" is synonymous with "$C_1$-$C_4$ alkyl," and is intended to embrace methyl (Me), ethyl (Et), propyl (Pr), n-propyl (nPr), isopropyl (iPr), butyl (Bu), n-butyl (nBu), isobutyl (iBu), sec-butyl (sBu), t-butyl (tBu), cyclopropyl (cyclPr), cyclobutyl (cyclBu), cyclopropyl-methyl (cyclPr-Me) and methyl-cyclopropane (Me-cyclPr), where the $C_1$-$C_4$ alkyl groups can be attached via any valence on the $C_1$-$C_4$ alkyl groups to the remainder of the molecule.

"Halo" refers to F, Cl, Br and I.

"Aryl" refers to an aromatic hydrocarbon, such as $C_6$-$C_{10}$ aromatic hydrocarbons including, but not limited to, phenyl and naphthyl.

"Aryloxy" refers to the group —O-aryl.

"Aralkyl" refers to the group -alkyl-aryl.

"Aryloxyalkyl" refers to the group -alkyl-O-aryl.

"Alkoxycarbonylalkyl" refers to the group -alkyl-(C=O)—O-alkyl.

"A pharmaceutically acceptable anion" when referring to a compound, indicates that the anion (labeled as $X^-$) is a counterion that is acceptable for use in humans, such as, for example, chloride, bromide, iodide, sulfate, methanesulfonate, benzenesulfonate, and toluenesulfonate.

The structures depicted in Formula I represent at least four possible stereoisomers incorporating the four possible isomers of the 7-azabicyclo[2.2.1]heptan-2-ol moieties as illustrated.

If additional stereo centers are present, for example, if for the group —C(R1)(R2)(R3), the carbon atom substituted by R1, R2, and R3 is asymmetric, a total of at least eight different diastereomers will result.

If the R4 and R5 groups are different, additional stereoisomers may be generated in the quaternization step.

The invention includes all active isomers, mixtures of active isomers, crystalline forms, amorphous forms, hydrates, or solvates of the subject compounds.

The chemical structures and chemical names listed herein are to be construed as including all isotopologues. Isotopologues are molecular entities that differ only in isotopic composition (number of isotopic substitutions), e.g. CH4, CH3D, CH2D2, etc., where "D" is deuterium, that is, 2H. Isotopologues can have isotopic replacements at any or at all atoms in a structure, or can have atoms present in natural abundance at any or all locations in a structure.

The term "diastereomers" refers to stereoisomers with two or more centers of dissymmetry and whose molecules are not minor images of one another.

The term "stereoisomers" refers to isomeric molecules that have the same molecular formula and connectivity of bonded atoms, but differ in the three-dimensional orientations of their atoms in space.

"Blending" refers to mixing different constituents to form a composition. Preferably the constituents are substantially uniformly distributed in the composition as determined by the constituent parts being no longer visually distinguishable from one another, by further blending not resulting in detectable increased uniformity, or by components being recoverable from random aliquots of a blend in proportions corresponding to the proportions of bulk reagents blended within expected tolerances for component recoveries. The resulting uniformity of a blend can be measured by relative standard deviation (RSD) of the active constituent(s), with a preferable relative standard deviation (RSD) being ≤5%.

Compounds are preferably provided in purified form i.e., at least partially separated from other components used in their production. A compound is preferably at least 80%, 90% 95%, or 99% pure or essentially homogeneous. Isolation percentages are preferably weight percent, but can also be mole percent. Components that are desired, such as pharmaceutically acceptable excipients or other compounds for use in a combination treatment are not included when calculating the percentage of purity of isolation.

A pharmaceutically acceptable excipient is approved or approvable by the FDA by current criteria for use in humans and is compatible with other ingredients of the composition.

A pharmaceutically acceptable salt is a salt approved or approvable by the FDA by current criteria for use in humans with compounds of Formula I.

A "stereochemically pure compound" contains primarily one stereoisomer out of two or more possible stereoisomers. A preparation of a stereochemically pure compound contains at least 80, 90, 95, 98, 99, 99.5 or 99.9% of a single stereoisomer of all stereoisomers of the compound present. Stereochemical purity percentages are preferably mole percent, but can also be weight percent.

Particle diameter is the diameter of a sphere of equal volume to a particle.

Fine particle dose (FPD) is the mass of drug deposited in a next generation impactor (NGI) device as described further below. Fine particle fraction (FPF) is the mass of drug deposited expressed as a percentage of the emitted dose.

VMD is the mean particle diameter in a composition.

X90 is the particle diameter at which 90% of particles in a composition have a smaller diameter. X50 is the median particle diameter at which 50% of particles in a composition have a smaller diameter and 50% larger. X10 is the median particle diameter at which 10% of particles in a composition have a smaller diameter and 90% larger.

RSD is the relative standard deviation of concentration (standard deviation/mean) between different samples of a composition and is a measure of extent of uniformity (smaller RSD means more uniform).

A "capsule" is a container enclosing an active pharmaceutical compound forming a barrier from the atmosphere, which can be opened, such as by piecing, to release the compound.

Hydroxypropyl methylcellulose (HPMC) is an exemplary material for a capsule.

A patient refers to a human or other animal to which the compositions of the present invention can be administered. Other animals include simians, avians, felines, canines, equines, rodents, bovines, porcines, ovines, caprines, mammalian farm animals, mammalian sport animals, and mammalian pets.

When various compositions or methods of the invention are described as comprising recited elements, meaning other elements may also be present, the invention should be understood as alternatively encompassing corresponding compositions or methods consisting of or consisting essentially of the recited elements.

"Consisting essentially of" is used in accordance with convention to allow inclusion of any unrecited materials or steps that do not materially affect the basic and novel characteristics of the composition or method.

"About" indicates insubstantial variation having no significant effect on the effectiveness or stability of a composition.

Unless otherwise apparent from the context, reference to an average can refer to any of the mean, median or mode.

Reference to a range should be understood as including reference to each integer bordering or within the range and all subranges formed from such integers.

"Herein" means anywhere in this patent document.

DETAILED DESCRIPTION

I. General

The invention provides pharmaceutical compositions including a compound of Formula I suitable for dispersal from a dried powder inhaler for treatment of asthma, COPD and other respiratory diseases. A compound of Formula I can be formulated as the only active compound or with a corticosteroid or other agent effective to treat respiratory conditions as a combination treatment.

II. Compounds of Formula I

Compounds of Formula I are anti-cholinergic compounds previously described in U.S. Pat. Nos. 8,742,131, 8,742,134 and 8,426,611 (each incorporated by reference). In brief, such a compound is a stereochemically pure M3 muscarinic acetylcholine receptor antagonist compound according to Formula I: A pharmaceutical composition comprising (a) a stereochemically pure M3 muscarinic acetylcholine receptor antagonist compound according to Formula I:

where R₁ is independently selected from phenyl or thienyl, both optionally substituted with an alkyl, alkoxy, halo, or COOR group; where R₂ is independently selected from phenyl, thienyl, cyclopentyl, cyclohexyl, 1-alkylcyclopentyl, 1-alkylcy-clohexyl, 1-hydroxycyclopentyl or 1-hydroxycyclohexyl, where phenyl, thienyl, cyclopentyl, cyclohexyl, 1-alkylcyclopentyl, 1-alkylcyclohexyl, 1-hydroxycyclopentyl or 1-hydroxycyclohexyl are optionally substituted with an alkyl, alkoxy, halo, or COOR group; or where R₁ and R₂ together are 9-xanthenyl, where 9-xanthenyl is substituted on either or both benzene rings with an alkyl, alkoxy, halo, or COOR group; where R₃ is OH; R₄ and R₅ are independently selected from lower alkyl, alkoxycarbonylalkyl, aralkyl, or aryloxyalkyl, where alkoxycarbonylalkyl and/or aralkyl are optionally substituted with an alkyl, alkoxy, halo, or COOR group; or R₄ and R₅ together with the ring to which they are attached form a five- or six-membered ring optionally substituted with aryl or aryloxy; where R is a lower alkyl; where *, , and * are each independently a stereocenter, and wherein the stereocenters *, , and * are present in one of the following combinations:

(i) * is (R),  is (R), and * is (S), or
(ii) * is (S),  is (S), and * is (R), or
(iii) * is (R),  is (S), and * is (R)
(iv) * is (S),  is (R), and * is (S); and

X⁻ represents a pharmaceutically acceptable anion, such as chloride, iodide, sulfate, methanesulfonate, benzenesulfonate, or toluenesulfonate.

Optionally, the stereochemically pure M3 muscarinic acetylcholine receptor antagonist compound according to Formula I is:

where R₁ is phenyl optionally substituted with alkyl, alkoxy, or halo groups;
R₂ is R₁, cyclopentyl, cyclohexyl, 1-alkylcyclopentyl or 1-alkylcyclohexyl;
R₃ is H or OH;
R₄ and R₅ are lower alkyl; and
X⁻ represents a pharmaceutically acceptable anion associated with the positive charge of the N atom, such as chloride, iodide, sulfate, methanesulfonate, benzenesulfonate, or toluenesulfonate.

More preferably, the stereochemically pure M3 muscarinic acetylcholine receptor antagonist compound is any of:

(1S,2R)-2-((R)-2'-cyclopentyl-2'-hydroxy-2'-phenylacetoxy)-7,7-dimethyl-7-azoniabicyclo[2.2.1]heptane bromide;

(1R,2S)-2-((R)-2'-cyclopentyl-2'-hydroxy-2'-phenylacetoxy)-7,7-dimethyl-7-azoniabicyclo[2.2.1]heptane bromide; or (1R,2R)-2-((R)-2'-cyclopentyl-2'-hydroxy-2'-phenylacetoxy)-7,7-dimethyl-7-azoniabicyclo[2.2.1]heptane bromide TRN-157 refers to the compound of IUPAC name of (1R,2S)-2-((R)-2'-cyclopentyl-2'-hydroxy-2'-phenylacetoxy)-7,7-dimethyl-7-azoniabicyclo[2.2.1]heptane bromide represented by formula (2) above.

III. Compositions of Compounds of Formula I

Compounds of Formula I are blended with lactose to form a formulation suitable for dispersal by a DPI. In some formulations, lactose is the only excipient and a compound of Formula I the only active agent included in a composition. Some compositions consist essentially of a compound of Formula I and lactose.

Although not preferred other excipients that may be present include calcium phosphate, magnesium stearate, talc, monosaccharides, disaccharides, starch, gelatin, cellulose, methyl cellulose, sodium carboxymethyl cellulose, dextrose, hydroxypropyl-1-cyclodextrin, polyvinylpyrrolidinone, low melting waxes, ion exchange resins, and the like, as well as combinations of any two or more thereof, as generally described "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

The particle diameter distribution of the compounds of Formula I and lactose and the ratio of the two can affect suitability of the composition for dispersal by a DPI. In general a smaller particle diameter for the active compound (e.g., 0.2-5 µm) is advantageous for dispersal to the deep peripheral airways of the lungs. However, fine particles of this size alone tend to adhere to one another causing aggregation and poor flowability. Aggregation can be reduced by including an excipient of larger particle size that adheres to the active compound during storage inhibiting aggregation but substantially detaches on actuation so that predominantly the active compound rather than excipient is dispersed throughout the lungs. Aggregation can also be reduced by reducing rugosity (surface roughness) of particles.

The particle diameter of the compound of Formula I preferably has an X90 of 3-4 μm and an X50 of 1-2 μm. Preferably, two-thirds, or about 80%, more preferably about 90% of the particles will have a diameter falling in the range of about 1 μm to about 5 μm. Such a particle diameter distribution can be achieved by milling such as described in the examples. A reduction in size so that most particles have a diameter between about 1 μm to about 5 μm is referred to as micronization.

The lactose is preferably an inhalation grade of lactose, preferably alpha-lactose monohydrate. Inhalation grades have typically undergone particle size reduction, such as by milling, and particle size selection to increase uniformity, such as by sieving. Such inhalation grade lactose is available from several commercial suppliers with various particle size distributions. Two such types of inhalation grade lactose are Respitose® SV003 (denoted herein Respitose) having a particle diameter X10 of 30 μm, an X50 of 59 μm and an X90 of 90 μm, and Lactohale® 200 (denoted herein Lactohale) having a particle diameter X10 of 9 μm, an X50 of 69 μm and an X90 of 141 μm, both from DFE Pharma. Some inhalation grades of lactose have a particle diameter characterized by X10 of 5-15 μm, an X50 of 50-100 μm and an X90 of 120-160 μm. The average particle diameter of the lactose is considerably larger than that of the compounds of Formula I in the present compositions.

After milling, the compound of Formula 1 is blended with lactose. Blending can be by manual or mechanical agitation, or a combination thereof, such as described in the examples. Preferably, the compound of Formula 1 and lactose are blended such that the compound of Formula I constitutes 0.025-4.0%, 0.025-2.0%, 0.05-2%, or 0.5-2%, 0.5-4.0% and optionally 0.05%, 0.5% or 2.0% by weight of the resulting composition. Preferably the relative standard deviation of the concentration of the compound of Formula 1 is ≤5%.

IV. Composition of Compounds of Formula I with a Corticosteroid

Compounds of Formula I can also be co-formulated with a corticosterioid, particularly mometasone for dispersal by a DPI. Mometasone refers to mometasone furoate, which is a glucocorticosteroid and has the IUPAC name of (11β,16α)-9,21-dichloro-11-hydroxy-16-methyl-3,20-dioxopregna-1, 4-dien-17-yl 2-furoate. Other corticosteroids that can be used include fluticasone propionate, budesonide, beclomethasone dipropionate, flunisolide, triamcinolone acetonide, or ciclesonide. As in compositions including only a compound of Formula I as the active agent, co-formulations also include lactose as the excipient. Some such compositions consist essentially of a compound of Formula I, a corticosteroid and lactose. Particle size and uniformity, order of blending compounds, and ratios of components can all affect suitability of the composition for dispersal as a DPI.

Both the compound of Formula I and the corticosteroid can be milled to achieve a particle diameter distribution within the ranges indicated above for the compound of Formula I.

The compound of Formula I and corticosteroid are preferably milled separately, and then individually blended with lactose, of the same types as described above, and then the two separate blends themselves blended to form a single composition. Preferably the relative standard deviation of concentration of each of the compound of Formula 1 and the corticosteroid is ≤5%. Alternative methods of blending, for example milling the compound of formula I such as TRN-157 and the corticosteroid such as mometasone together and then blending with lactose, were determined not to provide adequate uniformity of the blend.

Preferably, the corticosteroid constitutes 2-5% by weight of the composition, with the compound of Formula 1 constituting 0.025-4%, 0.025-2% or 0.05-2%, 0.5-4%, or 0.5-2% by weight of the composition as described before. In some compositions, the corticosteroid constitutes 2.2%-4.4% by weight of the composition. In some compositions, the compound of Formula I constitutes 0.05% and corticosteroid 4.4% by weight of the composition. In some compositions, the compound of Formula I constitutes 2.0% and the corticosteroid 2.2% by weight of the composition.

Collectively, the compound of Formula I and the corticosteroid have a fine particle fraction of at least 30%, preferably at least 40%, 45% or 50%, and most preferably at least 60%, 70%, or 75%. An exemplary range of fine particle fractions is 30-75% or 30-50%.

V. Stability

Compositions of the invention as described above are preferably stable at ambient temperature (i.e., within a range of about 20-23.5° C.) for at least a month, six months, a year or two years. Stability means that the activity of a compound of Formula I and corticosteroid (if present) after some period of time is greater than or equal to 95, 96, 97, 98 or 99% of its full activity, and/or that any byproducts formed during storage constitute less than 5, 3, 2 or 1 percent of the active compound (i.e., a compound of Formula I or corticosteroid) from which they were derived, and/or that the purity of the active compound remains greater than or equal to 95, 96, 97, 98, or 99% and/or that the FPF % decreases by no more than 15%, 10% or 5% of its value when the composition is formed.

VI. Dry Powder Inhaler

Dry powder inhalers (DPIs) are inhalers that deliver medication in a dry powder form. DPI medication is delivered by many different designs for inhalation. Examples of DPIs are: Accuhaler/Discus®, Aerohaler®, Aerolizer®, Clickhaler®, Diskhaler®, Easyhaler®, Handihaler®, Novolizer®, Pulvinal®, Rotadisk®, and Rotahaler®. Depending on the design, a DPI can be adapted to hold a single dose in a capsule, multiple individual doses in multiple capsules, for example, occupying different segments of a disk that rotates to introduce a different capsule into the operable position of the device, or a single capsule containing multiple undivided doses. DPI's can also be classified into: i) low-resistance devices (>90 L/min), ii) medium-resistance devices (about 60 L/min), and iii) high-resistance devices (about 30 L/min) based on the required inspiratory flow rates (L/min) which in turn depend on their design and mechanical features. The reported flow rates refer to the pressure drop of 4 kPa (kilopascal) in accordance with the European Pharmacopoeia.

The common feature of these devices is that the drug is in the form of a dry powder composition that undergoes dispersal into a patient's lungs driven by the patient's inhalation as distinct form a chemical propellant. DPI's have advantages of simplicity of use and avoiding propellants damaging to the environment, but have exacting requirements on a composition so that a drug is dispersed with sufficient uniformity and at a therapeutic dosage into the lungs of a patient without unacceptable clumping powered only by the patient's own inhalation.

VII. Treatment Indications, and Dosages

The compositions disclosed above can be used to treat patients having various respiratory diseases, particularly COPD and asthma, and also chronic bronchitis, chronic respiratory obstruction, pulmonary fibrosis, pulmonary emphysema, rhinorrhea, allergic rhinitis, and occupational lung diseases including pneumoconiosis (such as black lung disease, silicosis and asbestosis), acute lung injury (ALI), and acute respiratory distress syndrome (ARDS). Diagnosis can be according to formal guidelines, such as the National, Hear, Lung and Blood Institute Expert Panel Report 3: Guidelines for the Diagnosis and Management of Asthma (2007) or the Global Initiative for Chronic Obstructive Lung Disease Guidelines (2015), or based on any combination of signs and symptoms that in the opinion of a treating physician indicates sufficient likelihood of disease to justify treatment. Although an understanding of mechanism is not required for practice of the invention, it is believed that such diseases are mediated at least in part by muscarinic acetylcholine receptors.

Compositions are preferably manufactured under GMP conditions and are preferably sterile (United States Pharmacopeia Chapters 797, 1072, and 1211; California Business & Professions Code 4127.7; 16 California Code of Regulations 1751, 21 Code of Federal Regulations 211).

Compositions are administered in a regime effective to treat a respiratory disease. An effective regime represent a dose and frequency of administration effective to reduce severity or frequency or occurrence or inhibit or delay deterioration of at least one sign or symptom of the condition being treated.

Compositions can be administered on a recurring basis (e.g., 1, 2, 3, or 4 times per day, every other day, twice a week, weekly, every two weeks or monthly, regardless of the symptoms of the patient at the time of administration. Compositions can also be administered responsive to symptoms of the patient (i.e., a composition is administered as an outbreak of symptoms is approaching or occurring).

The dose for any particular patient depends on a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy.

Examples of dosages of the compounds described herein which can be used are an effective amount within the dosage range of about 0.1 µg to about 10 mg per kilogram of body weight or 0.001 mg to 100 mg, independently of body weight.

The present compositions can be administered in combination with any other conventional agents for treating respiratory disease. Other agents include other acetylcholine receptor inhibitors, such as ipratropium and tiotropium; or one or more anti-inflammatory, bronchodilator, antihistamine, decongestant or antitussive agents.

Although the invention has been described in detail for purposes of clarity of understanding, it will be obvious that certain modifications may be practiced within the scope of the appended claims. All publications, accession numbers, web sites, patent documents and the like cited in this application are hereby incorporated by reference in their entirety for all purposes to the same extent as if each were so individually denoted.

To the extent different information is associated with a citation at different times, the information present as of the effective filing date of this application is meant. The effective filing date is the date of the earliest priority application disclosing the accession number in question. Unless otherwise apparent from the context any element, embodiment, step, feature or aspect of the invention can be performed in combination with any other.

EXAMPLES

Example 1

Micronization of TRN-157 and Mometasone

The micronization of both TRN-157 and mometasone were performed in a Fluid Energy PE Jet-O-Mizer (Model 00) Jet Mill with Vibratory Feeder at a pressure of 120 psi under a nitrogen atmosphere.

Figure 1:
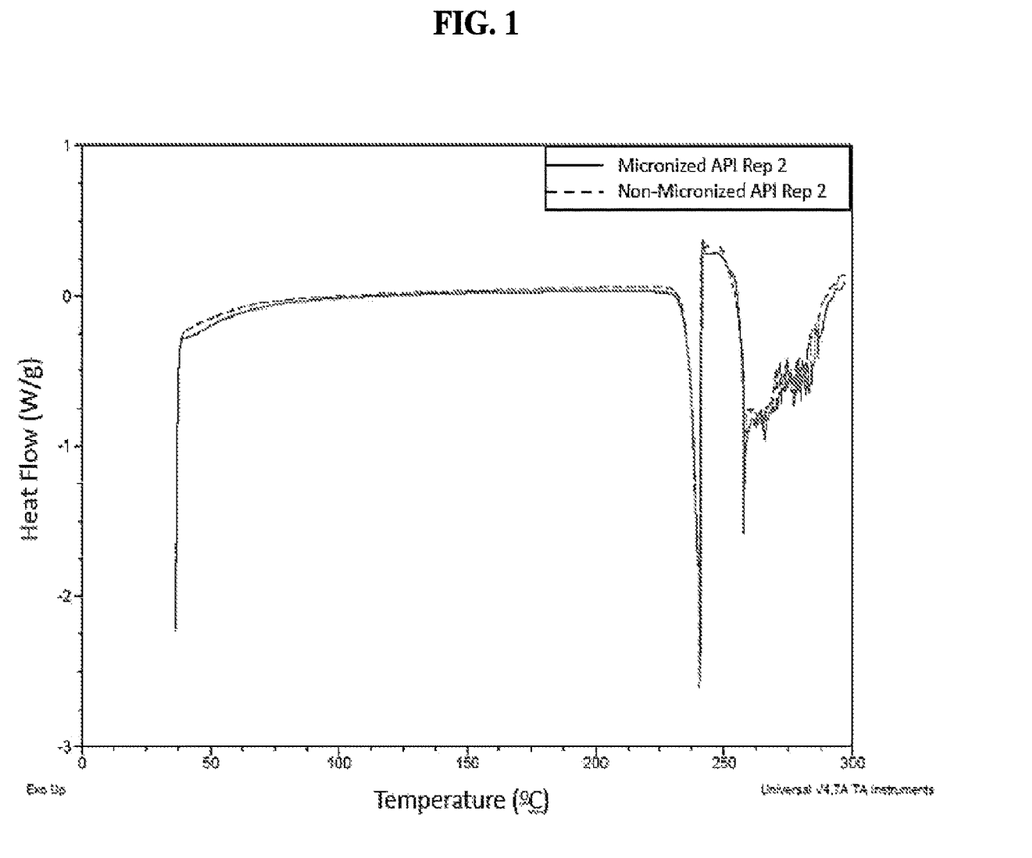
FIG. 1 shows thermogravimetric analysis (TGA) of TRN-157 micronized and non-micronized material. The similar pattern of both materials indicates no change in the physical structure of the material during micronization.

The TRN-157 or mometasone which had a starting particle size X50 of 12 µm and a X90 of 40 µm were transferred to the vibratory feeder in 3 g aliquots and micronized at a 1.5 g/min feed rate with precaution taken to ensure no particles clogged the lines, and the micronized material was collected in HDPE bottles. These bottles were tumbled to ensure a uniform distribution of particles. This process was repeated until the particle size averaged X50 of 1.93 µm and X90 of 3.94 µm, with little difference between replicates, as shown in Table 1. The analogous results for mometasone are shown in Table 2. The particle size distribution was determined by laser diffraction. No changes in chemical purity were detected after micronization using HPLC, and no changes in physical or chemical properties (e.g., crystal from) were detected by Thermogravimetric Analysis (FIG. 1).

TABLE 1

Particle size distribution of micronized TRN-157

| | Particle Size (µm) | | | |
|---|---|---|---|---|
| Replicate | X10 | X50 | X90 | VMD |
| 1 | 0.51 | 1.97 | 4.08 | 2.18 |
| 2 | 0.52 | 1.89 | 3.82 | 2.07 |

TABLE 1-continued

Particle size distribution of micronized TRN-157

| | Particle Size (μm) | | | |
|---|---|---|---|---|
| Replicate | X10 | X50 | X90 | VMD |
| 3 | 0.52 | 1.92 | 3.93 | 2.11 |
| Average | 0.52 | 1.93 | 3.94 | 2.12 |
| % RSD | 1.1 | 2.1 | 3.3 | 2.6 |

TABLE 2

Particle size distribution of micronized mometasone

| | Particle Size (μm) | | | |
|---|---|---|---|---|
| Replicate | X10 | X50 | X90 | VMD |
| 1 | 0.51 | 1.64 | 4.61 | 2.28 |
| 2 | 0.50 | 1.68 | 4.93 | 2.43 |
| 3 | 0.51 | 1.65 | 4.62 | 2.17 |
| Average | 0.51 | 1.66 | 4.72 | 2.29 |
| % RSD | 1.1 | 1.3 | 3.9 | 5.7 |

Example 2

The various blending experiments described herein utilized TRN-157 and mometasone micronized by the methods described above. The initial blending was performed using a spatula alternating addition of lactose and TRN-157 into a bottle. The bottle was then placed in a Turbula Type T2 F Shaker Mixer (Glen Mills) and blended for a total of 60 minutes. During this period the bottle was removed every 15 minutes, and tapped down to remove any powder accumulating at the cap. Samples were taken randomly from the blend and analyzed by HPLC to determine TRN-157 concentration for uniformity of blend. As seen in the first section of Table 4 below, good uniformity of concentration with % RSD=3.8% was achieved.

Example 3

The blending of TRN-157 and mometasone with lactose was initially performed by alternately mixing TRN-157, lactose, and mometasone using a spatula into a vessel. After the initial mixing, the mixture was transferred into a bottle and placed in the Turbula Type T2 F Shaker Mixer and blended for a total of 60 minutes. During this period the bottle was removed every 15 minutes, and tapped down to remove any powder accumulating at the cap. Samples were taken randomly and analyzed by HPLC to determine uniformity of blend. This procedure resulted in blends that were not uniform as evidenced by the high % RSD>5% as shown in Table 3. Prolonged mixing in the Turbula or a high sheer mixer did not result in improvement of % RSD.

TABLE 3

Uniformity of blend made by Procedure in Example 3

| Blend Description | Replicate | Wt Powder (mg) | TRN-157 Blend Assay Summary | | | | Mometasone Furoate Blend Assay Summary | | | |
|---|---|---|---|---|---|---|---|---|---|---|
| | | | Assay (ng/mL) | % wt/wt | Blend Avg | % RSD | Assay (μg/mL) | % wt/wt | Blend Avg | % RSD |
| 0.50% TRN-157/50 μg per Capsule | 1 | 21.152 | 122.89 | 0.5810 | 0.5801 | 5.9 | 8.550 | 4.04 | 4.077 | 5.4 |
| 4.4% Mometasone, 440 μg per Capsule | 2 | 19.200 | 119.37 | 0.6217 | | | 8.293 | 4.32 | | |
| 10 mg Fill Weight | 3 | 19.696 | 105.02 | 0.5332 | | | 7.498 | 3.81 | | |
| Lactohale LH200 | 4 | 20.333 | 123.97 | 0.6097 | | | 8.783 | 4.32 | | |
| 228-001-24-032 | 5 | 20.899 | 114.48 | 0.5478 | | | 8.062 | 3.86 | | |
| | 6 | 20.590 | 120.85 | 0.5869 | | | 8.478 | 4.12 | | |

Example 4

Another method was used to improve the uniformity of blend. The TRN-157 was blended with lactose in bottle A using a spatula alternating addition of lactose and TRN-157. Mometasone was blended in bottle B with lactose using a spatula similar to the TRN-157 blend. The contents of bottle A and B were blended into a third bottle C using a spatula initially and then placed in the Turbula mixer and blended for a total of 60 minutes. During this period the bottle was removed every 15 minutes, and tapped to remove any accumulating powder. Samples were taken randomly and analyzed by HPLC to determine uniformity of blend. The results are described in Example 5.

Example 5

Preparation and Uniformity of 2% TRN-157 and 2% TRN-157/4.4% Mometasone blends

The 2% TRN-157 blend was prepared following the procedure described in Example 2 using 400 mg of TRN-157 and 20 g of Lactohale® lactose accurately weighed out. At the end of 60 min six different 20 mg samples were taken. The samples were dissolved in 1 mL acetonitrile/water (1:1) and analyzed by HPLC for TRN-157 and quantified. This process resulted in uniform TRN-157 blends with % RSD ≤5%. The 2% TRN-157/4.4% mometasone blend was prepared following the procedure described in Example 4 using 400 mg of TRN-157, 880 mg of mometasone and 20 g of lactose accurately weighed out. At the end of 60 min, six different 20 mg samples were taken. The samples were dissolved in 1 mL acetonitrile/water (1:1) and analyzed by HPLC for both TRN-157 as well as mometasone. The results are tabulated in Table 4 below showing a TRN-157/mometasone blend with excellent uniformity of 2.3% for TRN-157 and 2.5% for mometasone.

TABLE 4

Blend uniformity using Lactohale ® 200 as carrier

| Blend Description | Blend Stage | Replicate | TRN-157 Blend Assay Summary | | | Mometasone Furoate Blend Assay Summary | | |
|---|---|---|---|---|---|---|---|---|
| | | | % wt/wt | Blend Avg | % RSD | % wt/wt | Blend Avg | % RSD |
| 2.0% TRN-157/200 μg per Capsule 10 mg Fill Weight | Initial | 1 | 1.8889 | 1.864 | 3.8 | | | |
| | | 2 | 1.8348 | | | | | |
| | | 3 | 1.8680 | | | | | |
| | | 4 | 1.7482 | | | | | |
| | | 5 | 1.9656 | | | | | |
| | | 6 | 1.8771 | | | | | |
| 2.0% TRN-157/200 μg per Capsule 4.4% Mometasone/440 μg per Capsule 10 mg Fill Weight | Initial | 1 | 2.1247 | 2.170 | 2.3 | 4.43 | 4.304 | 2.5 |
| | | 2 | 2.2019 | | | 4.27 | | |
| | | 3 | 2.2476 | | | 4.37 | | |
| | | 4 | 2.1352 | | | 4.39 | | |
| | | 5 | 2.1235 | | | 4.17 | | |
| | | 6 | 2.1857 | | | 4.20 | | |

Example 6

Aerodynamic Particle Size Determination by Next Generation Impactor

Testing to determine the performance of the blends in a DPI was performed on a Next Generation Impactor (NGI), MSP Model 170 with induction port and pre-separator inside a safetech environmental control chamber. The blends were loaded into the DPI device in HPMC capsules, size 3, loaded with 10 mg or 20 mg TRN-157, mometasone, and lactose blends. The device was actuated and the particles were dispersed after closing the controller and vacuum was applied. The particles travelled different distances based on the particle size and were collected in collection cups placed at appropriate distances. The cups corresponding to the 7 stages were collected and their contents analyzed using HPLC. The fine particle dose (FPD; total amount of drug in stages 3-7 with part of the amount in stage 2 corresponding to particles <4.6 μm diameter) and the fine particle fraction (FPF; FPD divided by emitted dose, as a percent) correspond to the amount of drug that would reach the human lung.

Example 7

The particle size distribution of TRN-157 blends with mometasone in two different lactose carriers were determined using the procedure described in Example 6. The results in Table 5 and Table 6 show that for TRN-157, the FPF was >30% (almost 40%) when Lactohale® 200 was used as carrier but was less than 30% with Respitose® SV003 as the carrier. The FPF for mometasone was also substantially improved (44% for Lactohale® vs 25% for Respitose®). Hence, Lactohale® 200 is an acceptable carrier but Respitose® SV003 is not.

TABLE 5

Particle size distribution with Respitose ® as carrier

| | TRN-157 (μg) | | | | | | | |
|---|---|---|---|---|---|---|---|---|
| Component, μg | NGI 1 | NGI 2 | NGI 3 | NGI 4 | NGI 5 | NGI 6 | Mean | % RSD |
| Capsule | 0.155 | 0.330 | 0.079 | 0.098 | 0.127 | 0.086 | 0.146 | |
| Device | 0.737 | 0.253 | 0.409 | 0.358 | 0.427 | 0.400 | 0.431 | |
| Throat | 0.652 | 0.359 | 0.853 | 0.620 | 0.702 | 0.840 | 0.804 | |
| Preseparator | 2.332 | 2.572 | 2.244 | 1.805 | 2.089 | 1.559 | 2.100 | |
| Stage 1 | 0.132 | 0.191 | 0.165 | 0.122 | 0.116 | 0.121 | 0.141 | |
| Stage 2 | 0.217 | 0.202 | 0.241 | 0.203 | 0.185 | 0.208 | 0.209 | |
| Stage 3 | 0.295 | 0.271 | 0.330 | 0.282 | 0.267 | 0.287 | 0.289 | |
| Stage 4 | 0.335 | 0.274 | 0.361 | 0.320 | 0.312 | 0.306 | 0.318 | |
| Stage 5 | 0.160 | 0.075 | 0.139 | 0.129 | 0.128 | 0.118 | 0.125 | |
| Stage 6 | 0.050 | 0.011 | 0.032 | 0.035 | 0.031 | 0.021 | 0.030 | |
| Stage 7 | 0.013 | 0.001 | 0.008 | 0.003 | 0.005 | 0.002 | 0.005 | |
| FPD, μg | 1.0 | 0.8 | 1.0 | 0.9 | 0.9 | 0.9 | 0.9 | 10.6 |
| FPF, % | 23.5 | 19.0 | 24.3 | 25.3 | 22.2 | 26.3 | 23.4 | 11.1 |

| | Mometasone (μg) | | | | | | | |
|---|---|---|---|---|---|---|---|---|
| Component, μg | NGI 1 | NGI 2 | NGI 3 | NGI 4 | NGI 5 | NGI 6 | Mean | % RSD |
| Capsule | 21.5 | 28.9 | 9.8 | 12.7 | 20.1 | 10.3 | 17.2 | |
| Device | 64.7 | 25.8 | 40.7 | 36.6 | 39.7 | 39.6 | 41.2 | |
| Throat | 53.8 | 34.0 | 59.2 | 52.7 | 56.6 | 53.4 | 51.6 | |
| Preseparator | 168.9 | 228.0 | 190.8 | 185.0 | 176.1 | 173.5 | 190.1 | |
| Stage 1 | 11.5 | 18.0 | 23.7 | 12.2 | 12.1 | 12.5 | 15.0 | |
| Stage 2 | 19.5 | 19.6 | 24.6 | 19.3 | 17.0 | 20.1 | 20.0 | |
| Stage 3 | 26.8 | 23.2 | 29.3 | 24.0 | 22.4 | 24.2 | 25.0 | |
| Stage 4 | 35.4 | 23.5 | 32.1 | 29.4 | 29.5 | 26.2 | 29.7 | |

TABLE 5-continued

| | Particle size distribution with Respitose ® as carrier | | | | | | | |
|---|---|---|---|---|---|---|---|---|
| Stage 5 | 21.2 | 7.5 | 15.3 | 15.6 | 15.5 | 13.4 | 14.7 | |
| Stage 6 | 8.0 | 1.3 | 4.3 | 5.0 | 4.9 | 3.5 | 4.5 | |
| Stage 7 | 2.6 | 0.4 | 0.8 | 1.0 | 1.2 | 0.5 | 1.1 | |
| FPD, μg | 106.6 | 67.5 | 101.3 | 88.4 | 83.6 | 81.7 | 87.9 | 16.1 |
| FPF, % | 28.9 | 19.1 | 28.3 | 25.1 | 24.9 | 24.8 | 24.9 | 12.9 |

TABLE 6

Particle size distribution with Lactohale ® as carrier

| | TRN-157 (μg) | | | | | | | |
|---|---|---|---|---|---|---|---|---|
| Component, μg | NGI 1 | NGI 2 | NGI 3 | NGI 4 | NGI 5 | NGI 6 | Mean | % RSD |
| Capsule | 0.178 | 0.189 | 0.130 | 0.191 | 0.118 | 0.174 | 0.200 | |
| Device | 0.929 | 0.920 | 0.791 | 1.186 | 0.925 | 1.028 | 1.000 | |
| Throat | 0.678 | 0.628 | 0.616 | 0.780 | 0.728 | 0.674 | 0.700 | |
| Preseparator | | | | 0.902 | 1.003 | 1.180 | 1.000 | |
| Stage 1 | 1.062 | 0.957 | 0.959 | 0.141 | 0.166 | 0.161 | 0.600 | |
| Stage 2 | 0.457 | 0.387 | 0.466 | 0.252 | 0.310 | 0.306 | 0.400 | |
| Stage 3 | 0.475 | 0.433 | 0.496 | 0.272 | 0.352 | 0.359 | 0.400 | |
| Stage 4 | 0.449 | 0.414 | 0.483 | 0.276 | 0.341 | 0.349 | 0.400 | |
| Stage 5 | 0.208 | 0.210 | 0.215 | 0.131 | 0.144 | 0.141 | 0.200 | |
| Stage 6 | 0.061 | 0.065 | 0.061 | 0.037 | 0.039 | 0.036 | 0.000 | |
| Stage 7 | 0.014 | 0.013 | 0.019 | 0.004 | 0.007 | 0.004 | 0.000 | |
| FPD, μg | 1.5 | 1.4 | 1.6 | 0.87 | 1.07 | 1.07 | 1.2 | 22.0 |
| FPF, % | 43.4 | 43.9 | 46.7 | 31.10 | 34.50 | 33.20 | 38.8 | 17.0 |

| | Mometasone (μg) | | | | | | | |
|---|---|---|---|---|---|---|---|---|
| Component, μg | NGI 1 | NGI 2 | NGI 3 | NGI 4 | NGI 5 | NGI 6 | Mean | % RSD |
| Capsule | 29.4 | 26.7 | 16.5 | 26.8 | 14.6 | 27.7 | 24.3 | |
| Device | 61.7 | 47.0 | 49.2 | 90.6 | 79.3 | 81.2 | 68.2 | |
| Throat | 61.0 | 57.2 | 56.2 | 65.2 | 65.3 | 59.8 | 60.8 | |
| Preseparator | | | | 80.5 | 101.8 | 98.8 | 93.7 | |
| Stage 1 | 60.6 | 55.0 | 71.9 | 14.4 | 17.0 | 15.4 | 39.0 | |
| Stage 2 | 46.9 | 39.5 | 45.1 | 26.8 | 31.3 | 31.0 | 36.8 | |
| Stage 3 | 44.1 | 40.1 | 41.7 | 30.9 | 35.3 | 36.1 | 38.0 | |
| Stage 4 | 38.5 | 36.1 | 38.1 | 36.0 | 35.6 | 38.0 | 37.1 | |
| Stage 5 | 22.3 | 22.6 | 19.6 | 19.9 | 16.6 | 17.0 | 19.7 | |
| Stage 6 | 8.1 | 10.0 | 7.1 | 6.3 | 4.9 | 4.7 | 6.8 | |
| Stage 7 | 2.0 | 2.4 | 2.4 | 1.4 | 1.5 | 1.0 | 1.8 | |
| FPD, μg | 143.2 | 134.9 | 135.4 | 110.3 | 112.8 | 115.1 | 125.3 | 11.3 |
| FPF, % | 50.4 | 51.2 | 48.0 | 39.2 | 36.4 | 38.1 | 43.9 | 15.3 |

Example 8

The particle size distribution of two TRN-157 blends with varying amount of Lactohale® lactose as carrier (10 mg and 20 mg) was determined by first making blends using the procedure described in Example 2 and then determining the particle size distribution following the procedure described in Example 6. The results showed a much higher fine particle fraction with 10 mg of lactose for 50 μg TRN-157 as shown in Tables 8 and 9. The better FPF for TRN-157 with 10 mg vs 20 mg lactose was also true in blends of TRN-157 with mometasone.

TABLE 8

TRN-157 blend with 20 mg Lactohale ®

| | TRN-157 (μg) | | | |
|---|---|---|---|---|
| Component, μg | NGI 1 | NGI 2 | NGI 3 | Mean |
| Capsule | 1.514 | 0.879 | 1.915 | 1.436 |
| Device | 8.130 | 8.393 | 15.560 | 10.694 |
| Throat | 6.280 | 7.436 | 6.115 | 6.610 |
| Preseparator | 17.820 | 17.339 | 16.300 | 17.153 |
| Stage 1 | 2.484 | 2.685 | 2.207 | 2.459 |
| Stage 2 | 3.433 | 3.372 | 3.263 | 3.356 |
| Stage 3 | 3.732 | 1.960 | 3.240 | 2.977 |
| Stage 4 | 3.588 | 3.291 | 2.865 | 3.248 |
| Stage 5 | 1.402 | 1.067 | 0.945 | 1.138 |
| Stage 6 | 0.469 | 0.317 | 0.213 | 0.333 |
| Stage 7 | 0.068 | 0.022 | 0.030 | 0.040 |
| FPD, μg | 11.32 | 8.67 | 9.22 | 9.7 |
| FPF, % | 28.8 | 23.1 | 26.2 | 26.0 |

TABLE 9

TRN-157 blend with 10 mg Lactohale ®

| | TRN-157 (μg) | | | |
|---|---|---|---|---|
| Component, μg | NGI 1 | NGI 2 | NGI 3 | Mean |
| Capsule | 2.610 | 1.996 | 2.278 | 2.295 |
| Device | 11.640 | 5.820 | 15.360 | 10.940 |
| Throat | 10.840 | 6.810 | 6.125 | 7.925 |
| Preseparator | 12.225 | 13.200 | 13.560 | 12.995 |
| Stage 1 | 2.036 | 2.280 | 2.237 | 2.184 |
| Stage 2 | 3.764 | 3.412 | 3.525 | 3.567 |
| Stage 3 | 4.004 | 4.624 | 4.398 | 4.342 |
| Stage 4 | 3.924 | 5.344 | 4.186 | 4.485 |
| Stage 5 | 1.560 | 1.922 | 1.300 | 1.594 |
| Stage 6 | 0.367 | 0.570 | 0.266 | 0.401 |
| Stage 7 | 0.085 | 0.075 | 0.020 | 0.060 |
| FPD, μg | 12.15 | 14.53 | 12.22 | 12.96 |
| FPF, % | 31.3 | 38.0 | 34.3 | 34.5 |

Example 9

Blend Stability

Figure 2A:
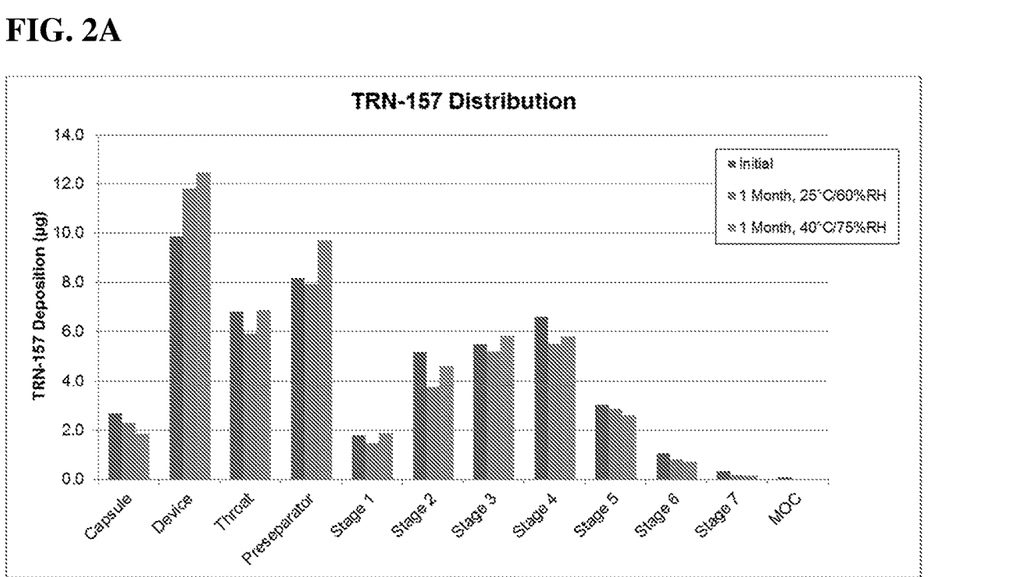
FIGS. 2A-B show particle size distribution of TRN-157 and mometasone in blends kept under normal (25° C./60% RH) and accelerated (40° C./75% RH) stability conditions, as determined with a New Generation Impactor (NGI), showing no significant change after 1 month in either condition.
Figure 2B:
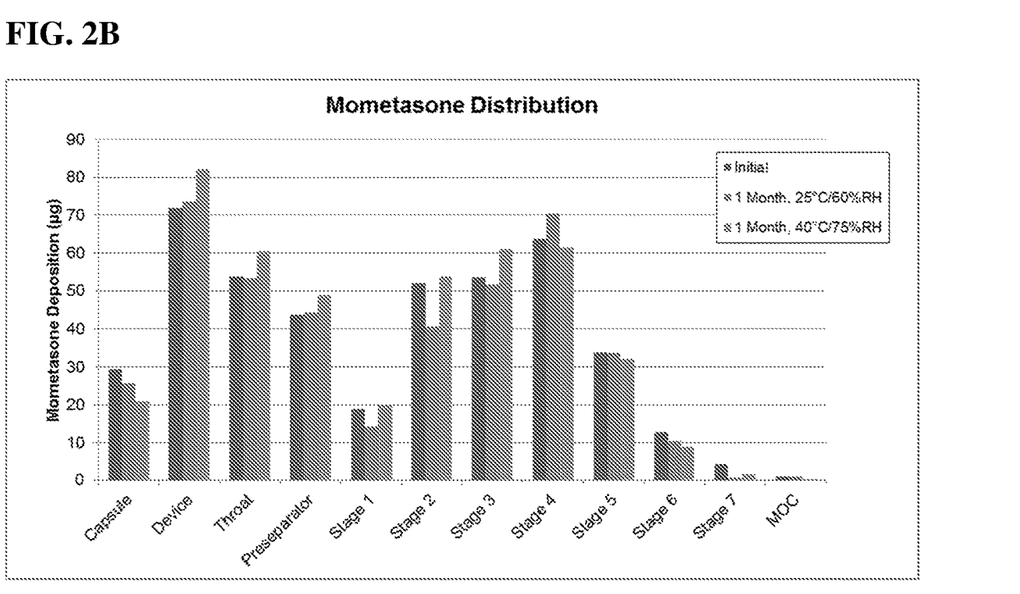

The stability study looks at both the chemical stability of TRN-157 as well as mometasone, and physical properties such as appearance, particle size distribution and water content. The different blends with varying amounts of TRN-157 and mometasone were made using the procedure described in Example 2 and Example 4. The blends were then placed in a chamber with controlled temperature and humidity. Capsules are then taken out at different preset time points (1 week, 2 weeks, 1 month, 3 months etc.) and the samples analyzed by HPLC and compared to the original material to determine extent of degradation. The particle size distribution is also determined following the procedure described in Example 6. The results showed that the blends were very stable at room temperature all the way up to 80° C. for at least 2 weeks as exemplified in Table 10. The particle size distribution was also unchanged after 1 month at all temperatures and humidity conditions tested as shown in Table 11 and illustrated in FIGS. 2A-B. Interestingly, the FPF for TRN-157 was improved when it was in a blend with mometasone relative to when used alone from 35-40% to >60% and the FPF for mometasone was also high at >60% (see FPF at initial time points in Table 11). Without being bound by theory, it is believed that the TRN-157 and mometasone may interact and serve as additional carriers for each other.

TABLE 10

Stability of TRN-157/Mometasone blends at various temperature conditions.

| | | TRN-157 (%) | | | | | | |
|---|---|---|---|---|---|---|---|---|
| | | Original Analysis in August | | 1 Week | | | 2 Week | | |
| Blend ID | Condition | Individual | Average | Individual | Average | % Relative to original | Individual | Average | % Relative to original |
| 0.075% TRN-157 228-001-10-041 | 25° C./60% RH | 0.0720 0.0722 0.0689 | 0.0712 | 0.0732 0.0728 0.0721 | 0.0727 | 102.1 | 0.0709 0.0725 0.0705 | 0.0713 | 100.1 |
| | 60° C. | | | 0.0726 0.0719 0.0720 | 0.0722 | 101.4 | 0.0743 0.0736 0.0728 | 0.0736 | 103.3 |
| | 80° C. | | | 0.0707 0.0718 0.0688 | 0.0708 | 99.4 | | | |
| 0.075% TRN-157 0.3% Mometasone 228-001-10-042 | 25 C./60% RH | 0.0745 0.0746 0.0723 | 0.0734 | 0.0709 0.0740 0.0717 | 0.0722 | 98.4 | 0.0743 0.0736 0.0724 | 0.0734 | 100.0 |
| | 60 C. | | | 0.0796 0.0748 0.0837 | 0.0794 | 108.2 | 0.0746 0.0745 0.0736 | 0.0742 | 101.1 |
| | 80 C. | | | 0.0712 0.0721 0.0672 | 0.0702 | 95.6 | | | |
| 0.8% TRN-157 228-001-10-045 | 25 C./60% RH | 0.807 0.794 0.799 | 0.800 | 0.774 0.782 0.794 | 0.7833 | 98.0 | 0.785 0.806 | 0.796 | 99.5 |
| | 60 C. | | | 0.792 0.810 0.801 | 0.8010 | 100.2 | 0.816 0.794 0.799 | 0.803 | 100.4 |
| | 80 C. | | | 0.777 0.790 0.778 | 0.7817 | 97.8 | | | |
| 0.8% TRN-157 3.2% Mometasone 228-001-10-046 | 25 C./60% RH | 0.797 0.824 0.796 | 0.798 | 0.792 0.786 0.799 | 0.7923 | 99.2 | 0.800 0.794 | 0.797 | 99.8 |
| | 60 C. | | | 0.780 0.786 0.784 | 0.7833 | 98.1 | 0.822 0.815 | 0.819 | 102.5 |
| | 80° C. | | | 0.777 0.789 0.795 | 0.7870 | 96.6 | | | |

TABLE 11

Particle size distribution stability at various temperature conditions

| Formulation | Time Point | Condition | Replicate | TRN-157 FPD, μg | TRN-157 FPF, % | Mometasone FPD, μg | Mometasone FPF, % |
|---|---|---|---|---|---|---|---|
| 2.0% TRN-157/200 μg ID: 228-001-24-063 | Initial | NA | 1 | 52.21 | 36.8 | | |
| | | | 2 | 75.78 | 43.6 | | |
| | | | 3 | 70.10 | 35.6 | | |
| | 1 Month | 25° C./60% RH | 1 | 52.83 | 42.6 | | |
| | | | 2 | 59.12 | 41.1 | | |
| | | | 3 | 72.99 | 42.1 | | |
| | | 40° C./75% RH | 1 | 46.26 | 37.6 | | |
| | | | 2 | 50.49 | 38.4 | | |
| | | | 3 | 76.84 | 41.1 | | |
| 2.0% TRN-157/200 μg 4.4% Mometasone/440 μg ID: 228-001-24-065 | Initial | NA | 1 | 88.14 | 61.4 | 196.8 | 63.2 |
| | | | 5 | 95.56 | 61.7 | 207.2 | 61.4 |
| | | | 6 | 101.54 | 63.9 | 224.4 | 64.2 |
| | 1 Month | 25° C./60% RH | 1 | 87.36 | 62.7 | 203.4 | 60.8 |
| | | | 2 | 105.95 | 63.3 | 247.3 | 63.6 |
| | | | 3 | 81.62 | 62.8 | 204.0 | 63.5 |
| | | 40° C./75% RH | 1 | 95.82 | 59.6 | 217.0 | 61.1 |
| | | | 2 | 86.19 | 56.5 | 213.6 | 58.3 |
| | | | 3 | 67.24 | 54.6 | 181.6 | 58.2 |

Additional blends listed in Table 12 below are also part of the stability study at 25° C./60% RH and 40° C./75% RH conditions and are being evaluated for chemical stability and particle size distribution at regular time points; to date the results are comparable to those shown in Tables 11 and 12.

TABLE 12

Blends being evaluated for stability
Formulation 0.050% TRN-157/5 μg
ID: 228-001-24-062
2.0% TRN-157/200 μg
ID: 228-001-24-063
0.05% TRN-157/5 μg
4.4% Mometasone/440 μg
ID: 228-001-24-067
0.5% TRN-157/50 μg
4.4% Mometasone/440 μg
ID: 228-001-24-064
2.0% TRN-157/200 μg
2.2% Mometasone/220 μg
ID: 228-001-24-066
2.0% TRN-157/200 μg
4.4% Mometasone/440 μg
ID: 228-001-24-065

The blends, which are powders, are being stored in capsules of the type used in DPI devices. After 12 months storage at 25° C./60% RH, the powder in the capsules was physically stable as it remained a white, free-flowing powder with no agglomeration or foreign particulates. Karl Fischer analysis of the blends provided an initial water content of ~4.8% (coming primarily from the lactose carrier). The water content was within 0.6% of the initial time point for all blends after 12 months, indicating no significant water absorption. All blends were extremely chemically stable, with all peaks representing related substances (e.g., degradants) either not detected, below the limit of quantitation, or ≤0.1% at all time points. The delivered dose from an RS01 capsule DPI (Plastiape) measured at 100 LPM with a critical flow controller time of 2.4 sec to pull 4 L of air was ~70% for the different blends, and there was no trend toward a decrease during the 12-month stability period. The aerodynamic particle size distribution was comparable for TRN-157 and mometasone in the various blends at about 2.4 μm, and increased at most slightly at 12 months, e.g. by 0.4 μm. The following Tables 13 and 14 show the FPF for TRN-157 and mometasone for each blend at each time point (25° C./60% RH storage), measured with a 7-stage NGI and pre-separator. While the results varied somewhat between the different blends (especially regarding the initial time point), in general there was only about a 10% or less reduction from the initial to final 12-month time point.

TABLE 13

Stability of TRN-157 in blends

| Formulation | | Initial | 1 month | 3 months | 6 months | 9 months | 12 months |
|---|---|---|---|---|---|---|---|
| TRN-157 | Mometasone | FPF (%) | FPF (%) | FPF (%) | FPF (%) | FPF (%) | FPF (%) |
| 0.05% | — | 22.9 | 19.6 | 18.8 | 19.6 | 18.9 | 18 |
| 2.0% | — | 38.6 | 41.9 | 40.9 | 39.4 | 38.2 | 36.2 |
| 2.0% | 2.2% | 63.7 | 55.4 | 55.9 | 51.4 | 49 | 53.1 |
| 0.05% | 4.4% | 28.5 | 35.8 | 41.1 | 41.1 | 39.3 | 32.2 |
| 0.5% | 4.4% | 50.9 | 49.7 | 47.5 | 46.8 | 47 | 44.2 |
| 2.0% | 4.4% | 62.3 | 62.9 | 60.8 | 59 | 51.1 | 56.7 |

TABLE 14

| Stability of Mometasone in blends | | | | | | | |
|---|---|---|---|---|---|---|---|
| Formulation | | Initial | 1 month | 3 months | 6 months | 9 months | 12 months |
| TRN-157 | Mometasone | FPF (%) | FPF (%) | FPF (%) | FPF (%) | FPF (%) | FPF (%) |
| 0.05% | — | Not applicable | | | | | |
| 2.0% | — | Not applicable | | | | | |
| 2.0% | 2.2% | 60.9 | 59 | 57.1 | 55.6 | 53.8 | 54.2 |
| 0.05% | 4.4% | 39.2 | 43.3 | 44 | 46 | 44.6 | 40 |
| 0.5% | 4.4% | 59.2 | 56.6 | 57.9 | 58.7 | 55.8 | 56.1 |
| 2.0% | 4.4% | 62.9 | 62.6 | 62.7 | 62.8 | 58.8 | 57.9 |

Although the invention has been described with reference to the presently preferred embodiments, it should be understood that various modifications can be made without departing from the invention. Unless otherwise apparent from the context any step, element, embodiment, feature or aspect of the invention can be used with any other. All publications, patents and patent applications including accession numbers and the like cited are herein incorporated by reference in their entirety for all purposes to the same extent as if each individual publication, patent and patent application was specifically and individually indicated to be incorporated by reference in its entirety for all purposes. The word "herein" shall indicate anywhere in this patent application, not merely within the section where the word "herein" occurs.

What is claimed is:

1. A pharmaceutical composition comprising (a) a stereochemically pure M3 muscarinic acetylcholine receptor antagonist compound selected from the group consisting of wherein

X⁻ represents a pharmaceutically acceptable anion;

(b) sieved inhalation grade lactose having a particle diameter distribution characterized by an X10 of 1-15 µm, an X50 of 50-100 µm and an X90 of 120-160 µm; and

(c) a corticosteroid;

wherein the compound constitutes 0.025 to 4% by weight of the pharmaceutical composition, the corticosteroid constitutes 2-5% by weight of the pharmaceutical composition and the compound, corticosteroid and lactose are in a blend, wherein the composition is dispersible from a dried powder inhaler, wherein the blend of the compound in lactose has a fine particle fraction (FPF) of ≥50%.

2. The pharmaceutically acceptable composition of claim 1, wherein the stereochemically pure M3 muscarinic acetylcholine receptor antagonist compound is selected from the group consisting of:

(1S,2R)-2-((R)-2'-cyclopentyl-2'-hydroxy-2'-phenylacetoxy)-7,7-dimethyl-7-azoniabicyclo[2.2.1]heptane bromide;

(1R,2S)-2-((R)-2'-cyclopentyl-2'-hydroxy-2'-phenylacetoxy)-7,7-dimethyl-7-azoniabicyclo[2.2.1]heptane bromide; and (1R,2R)-2-((R)-2'-cyclopentyl-2'-hydroxy-2'-phenylacetoxy)-7,7-dimethyl-7-azoniabicyclo[2.2.1]heptane bromide.

3. A pharmaceutical composition according to claim 1, where X⁻ is selected from the group consisting of chloride, bromide, iodide, sulfate, methanesulfonate, benzenesulfonate, and toluenesulfonate.

4. The pharmaceutical composition of claim 1, wherein the lactose has a particle diameter distribution characterized by an X10 of 9 µm, an X50 µm of 69 and an X90 of 141 µm.

5. The pharmaceutical composition of claim 1, wherein the compound has a particle diameter distribution characterized by an X90≤4.5 µm.

6. The pharmaceutical composition of claim 5, wherein the particle diameter distribution is further characterized an X50≤2.5 µm.

7. The pharmaceutical composition of claim 1, wherein the compound constitutes 0.025 to 2.0% by weight of the composition.

8. The pharmaceutical composition of claim 7, wherein the compound constitutes 0.05% by weight of Formula I.

9. The pharmaceutical composition of claim 1, wherein the corticosterioid is mometasone.

10. The pharmaceutical composition of claim 9, wherein the mometasone has a particle diameter distribution characterized by an X90 of ≤4 µm.

11. The pharmaceutical composition of claim 10, wherein the particle diameter distribution is further characterized by an X50 of ≤2 µm.

12. The pharmaceutical composition of claim 9, wherein the mometasone and compound are blended to a uniformity characterized by a relative standard deviation of ≤5%.

13. The pharmaceutical composition of claim 9, wherein the mometasone constitutes 2.2-4.4% by weight of the composition.

14. The pharmaceutical composition of claim 7, wherein the compound constitutes 0.05% and mometasone 4.4% by weight of the composition.

15. The pharmaceutical composition of claim 7 wherein the compound constitutes 2.0% and mometasone 2.2% by weight of the composition.

16. The pharmaceutical composition of claim 1 consisting essentially of the compound, lactose and mometasone.

17. A capsule comprising the pharmaceutical composition of claim 1, the capsule adapted for insertion in a dry powder inhaler wherein the composition can be dispersed into the lungs of a subject.

18. A dry powder inhaler comprising a pharmaceutical composition according to claim 1.

19. A process for preparing a pharmaceutical composition of claim 9, comprising: (a) micronizing the compound until the volume mean diameter (VMD) is less than 5 µm, (b) blending the micronized compound with lactose to make composition I, (c) micronizing mometasone until the VIVID is less than 5 µm, (d) blending mometasone with lactose to make composition II, and (e) combining the blended compositions I and II to make a final blend.

20. A method of treating a patient with asthma or COPD comprising administering to the patient a therapeutically effective amount of a pharmaceutical composition of claim 1 from a dry powder inhaler.

* * * * *